US009936866B2

(12) United States Patent
Lemonis et al.

(10) Patent No.: US 9,936,866 B2
(45) Date of Patent: Apr. 10, 2018

(54) ADJUSTING LASER TREATMENT IN RESPONSE TO CHANGES IN THE EYE

(71) Applicant: Novartis AG, Basel (CH)

(72) Inventors: Sissimos Lemonis, Schwaig (DE); Mario Abraham, Burgthann (DE)

(73) Assignee: Novartis AG (CH)

( * ) Notice: Subject to any disclaimer, the term of this patent is extended or adjusted under 35 U.S.C. 154(b) by 482 days.

(21) Appl. No.: 14/389,725

(22) PCT Filed: Sep. 24, 2013

(86) PCT No.: PCT/EP2013/069791
§ 371 (c)(1),
(2) Date: Sep. 30, 2014

(87) PCT Pub. No.: WO2015/043616
PCT Pub. Date: Apr. 2, 2015

(65) Prior Publication Data
US 2015/0148788 A1    May 28, 2015

(51) Int. Cl.
*A61B 3/00*     (2006.01)
*A61F 9/008*    (2006.01)
*A61B 3/11*     (2006.01)
*A61B 3/117*    (2006.01)
*A61B 3/113*    (2006.01)

(52) U.S. Cl.
CPC ............ *A61B 3/0025* (2013.01); *A61B 3/112* (2013.01); *A61B 3/117* (2013.01); *A61F 9/008* (2013.01); *A61F 9/00804* (2013.01); *A61F 9/00827* (2013.01); *A61B 3/113* (2013.01); *A61F 9/0084* (2013.01); *A61F 9/00814* (2013.01); *A61F 2009/00844* (2013.01); *A61F 2009/00846* (2013.01); *A61F 2009/00851* (2013.01); *A61F 2009/00882* (2013.01); *A61F 2009/00897* (2013.01)

(58) Field of Classification Search
CPC ....... A61B 3/0025; A61B 3/112; A61B 3/113; A61F 9/008; A61F 2009/008
USPC ........................................................... 606/5
See application file for complete search history.

(56) References Cited

U.S. PATENT DOCUMENTS 5,807,381 A    9/1998  Lieberman
6,802,837 B2   10/2004 Donitzky et al.
(Continued)

FOREIGN PATENT DOCUMENTS

EP        1985269 A1    10/2008
WO     2009135084 A1    11/2009
WO     2012040196 A1     3/2012

*Primary Examiner* — Gary Jackson
*Assistant Examiner* — Zahed Kabir
(74) *Attorney, Agent, or Firm* — Keiko Ichiye

(57) ABSTRACT

According to certain embodiments, a system comprises one or more memories and one or more processors. The one or more memories store optical data from an optical recorder comprising at least two optical data sets by: receiving a first optical data set of an eye with a pupil having a first pupil size; and receiving a second optical data set of the eye with the pupil having a second pupil size. The one or more processors determine a pseudo-rotation related to a pupil size change, receive a measured cyclotorsion, calculate an actual cyclotorsion from the measured cyclotorsion and the pseudo-rotation, and adjust a laser treatment according to the actual cyclotorsion.

22 Claims, 5 Drawing Sheets

(56) References Cited

U.S. PATENT DOCUMENTS

| | | | |
|---|---|---|---|
| 7,044,602 B2* | 5/2006 | Chernyak | A61B 3/1015 351/205 |
| 2003/0223037 A1 | 12/2003 | Chernyak | |
| 2005/0024586 A1* | 2/2005 | Teiwes | A61B 3/113 351/209 |
| 2005/0137586 A1 | 6/2005 | Gray et al. | |
| 2009/0275929 A1* | 11/2009 | Zickler | A61B 3/113 606/5 |
| 2010/0211054 A1 | 8/2010 | Lemonis | |
| 2012/0242956 A1* | 9/2012 | Chernyak | A61B 3/112 351/210 |
| 2015/0116725 A1* | 4/2015 | Lemonis | A61F 9/00802 356/479 |

* cited by examiner

ADJUSTING LASER TREATMENT IN RESPONSE TO CHANGES IN THE EYE

CROSS REFERENCE TO RELATED APPLICATIONS

This application is a section 371 national stage phase of International Application No. PCT/EP2013/069791, filed 24 Sep. 2013, titled "ADJUSTING LASER TREATMENT IN RESPONSE TO CHANGES IN THE EYE," which is hereby incorporated by reference in its entirety.

TECHNICAL FIELD

The present disclosure relates generally to ophthalmic surgical systems, and more particularly to adjusting laser treatment in response to changes in the eye.

BACKGROUND

Laser treatment systems typically center a treatment profile on a particular portion of the eye, such as the pupil center. The eye, however, changes in a variety of ways, and these changes may move that portion. For example, movement of the eyeball itself may move the portion. As another example, changes in the iris under different light conditions may move the portion. Accordingly, the systems should compensate for the movement of the portion in order to properly apply the treatment.

BRIEF SUMMARY

According to certain embodiments, a method includes storing, by one or more memories, optical data from an optical recorder comprising at least two optical data sets by: gathering a first optical data set of an eye with a pupil having a first pupil size; and gathering a second optical data set of the eye with the pupil having a second pupil size. One or more processors determine a pseudo-rotation related to a pupil size change, receive a measured cyclotorsion, calculate an actual cyclotorsion from the measured cyclotorsion and the pseudo-rotation, and adjust a laser treatment according to the actual cyclotorsion.

According to certain embodiments, a system comprises one or more memories and one or more processors. The one or more memories store optical data from an optical recorder comprising at least two optical data sets by: receiving a first optical data set of an eye with a pupil having a first pupil size; and receiving a second optical data set of the eye with the pupil having a second pupil size. The one or more processors determine a pseudo-rotation related to a pupil size change, receive a measured cyclotorsion, calculate an actual cyclotorsion from the measured cyclotorsion and the pseudo-rotation, and adjust a laser treatment according to the actual cyclotorsion.

BRIEF DESCRIPTION OF THE DRAWINGS

Exemplary embodiments of the present disclosure will now be described by way of example in greater detail with reference to the attached figures, in which.

DESCRIPTION OF EXAMPLE EMBODIMENTS

Figure 1:
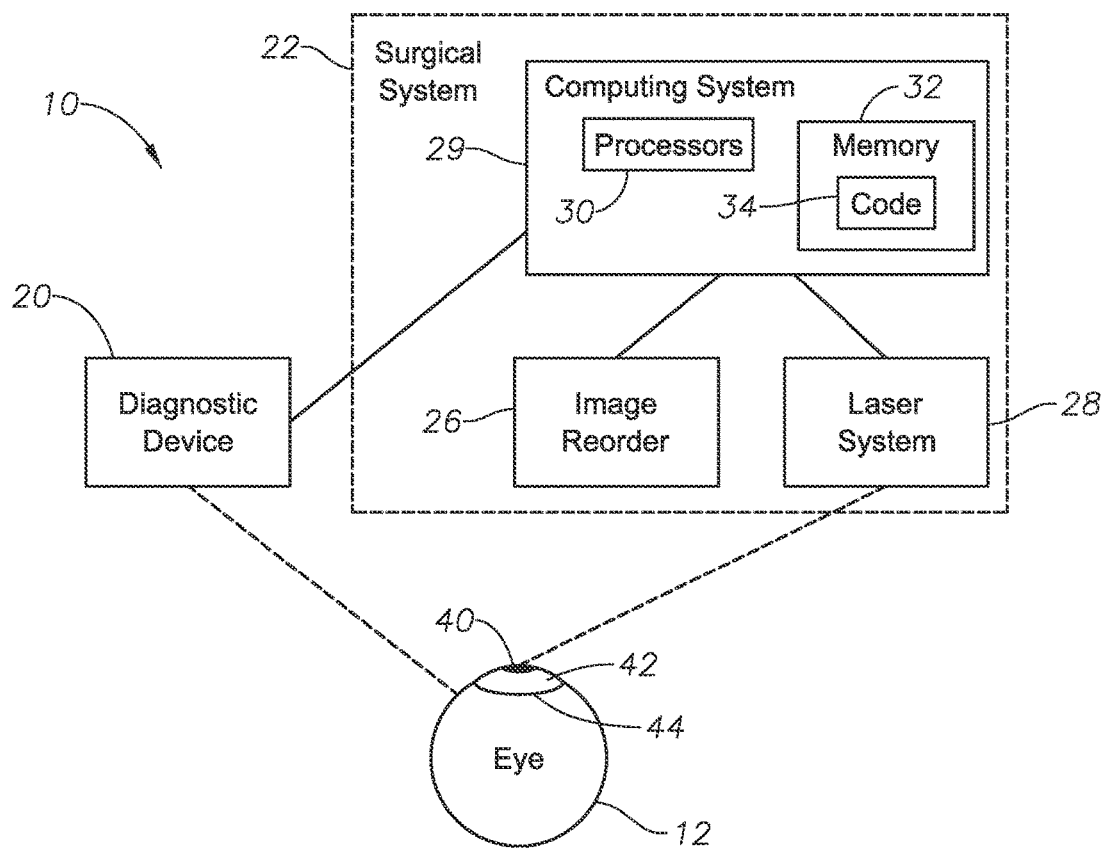
FIG. 1 illustrates an example of a system that can adjust laser treatment in response to changes in the eye according to certain embodiments.

Referring now to the description and drawings, example embodiments of the disclosed apparatuses, systems, and methods are shown in detail. The description and drawings are not intended to be exhaustive or otherwise limit or restrict the claims to the specific embodiments shown in the drawings and disclosed in the description. Although the drawings represent possible embodiments, the drawings are not necessarily to scale and certain features may be exaggerated, removed, or partially sectioned to better illustrate the embodiments.

FIG. 1 illustrates an example of a system 10 that can adjust laser treatment in response to changes in the eye according to certain embodiments. In the illustrated embodiment, system 10 includes a diagnostic device 20 and a surgical system 22 that provide services for a target such as an eye 12. Surgical system 22 includes a computing system 24, an optical recorder 26, and a laser system 28. Computing system 24 includes one or more processors 30 and a memory 32 that can store logic such as code 34. Computing system 24 is in communication with diagnostic device 20, optical recorder 26, and laser system 28.

Eye 12 has physical features, such as a pupil 40, an iris 42, and a limbus 44. An eye feature has a location ("feature location"), which may be expressed in any suitable manner, for example, using Cartesian, polar, or spherical coordinates. An eye feature also has a size ("feature size"), which may be expressed in any suitable manner, for example, as a feature dimension (such as a feature minor axis, feature major axis, feature width, and/or feature height) and/or other feature measurement (such as a feature circumference). For example, pupil 40 has a pupil size, which may be expressed as a pupil minor axis, pupil major axis, pupil width, and/or pupil height) and/or other pupil measurement, such as a pupil circumference.

Eye 12 changes in a variety of ways. For example, the eyeball itself moves. Eye 12 can spin generally about its optical axis (which may approximate a z-direction), also known as "cyclotorsion." Eye 12 can also roll about an axis parallel to the body's longitudinal axis (which may approximate a y-direction), or about an axis parallel to the body's transverse axis (which may approximate an x-direction). In addition, eye 12 can move in a translational motion in any suitable direction.

As another example, iris 42 changes the size of pupil 40 to regulate the amount of light that enters the interior of eye 12. A change in the pupil size is typically not concentric, so the change typically displaces the center of pupil 40, which is known as "pupil center shift". Moreover, as iris 42 changes, structures of iris 42 move and may give the appearance that the whole eyeball is rotating. Herein, this effect is called "pseudo-rotation." Pseudo-rotation may be regarded as a "fake" rotation of eye 12 in that the whole eye 12 is not rotating but rather just appears to be rotating, while cyclotorsion may be regarded as a "real" or actual rotation of eye 12.

Certain known eye tracking systems track pseudo-rotation as a real rotation and adjust the ablation profile as if the pseudo-rotation were real. Since the pseudo-rotation is not real, however, the adjustment results in an incorrect placement of the ablation profile. To avoid this problem, system 10 distinguishes pseudo-rotation from real rotation. In certain embodiments, system 10 measures the pupil under different illumination and thus different sizes (e.g., scotopic, mesopic, and/or photopic) to see how the eye changes in response to illumination versus real rotation. For example, system 10 may detect how an iris feature changes in response to different illumination. This feature change may be regarded as a result of pseudo-rotation, not real rotation, and thus maybe used to distinguish pseudo-rotation from real rotation.

In certain embodiments, diagnostic device 20 and/or surgical system 22 perform actions for eye 12 that may require precise alignment with eye 12 and may track a particular feature of eye 12 for alignment. As discussed above, however, eye 12 changes, and these changes may move the tracked portion. Accordingly, computing system 24 may adjust treatment to compensate for the movement resulting from changes in eye 12. In certain embodiments, diagnostic device 20 measures eye 12 and features of eye 12 to yield diagnostic data that include the measurements. Examples of diagnostic device 20 include optical coherence tomography (OCT), optical low-coherence reflectometry (OLCR), pupil meter, Placido, topography, wavefront, and optical axial length measuring and/or analyzing systems. In certain embodiments, surgical system 22 performs laser surgery on eye 12, such as LASIK, EPI-LASIK, lenticule extraction, or PRK surgery. In some situations, diagnostic device 20 measures eye 12 when pupil 40 is at one size, and surgical system 22 performs laser surgery on eye 12 when pupil 40 is at a different size, due to, e.g., different lighting conditions.

Optical recorder 26 may be any suitable device that records radiation reflected from an object as optical data, which can be used to generate an image of the object. For example, optical recorder 26 may be a camera that has an array of photodetectors that detect reflected light from an object. As another example, optical recorder 26 may be an eye tracking device that tracks features of eye 12 in order to detect movement of eye 12. As yet another example, optical recorder 26 may be an OCT, OLCR, or a skiascopy device. In certain embodiments, optical recorder 26 detects light to generate optical data that comprise at least two optical data sets. An optical data set may include data captured at one time by a photodetector array when the pupil has a particular pupil size. Optical recorder 26 may send the optical data to computing system 24. In certain embodiments, the same IR illumination from a diagnostic device and an eye tracker device may be used to increase the accuracy in detecting the iris-sclera border.

In certain embodiments, computing system 24 calculates from the optical data an adjustment to a laser treatment. Computing system 24 may use a compensation operation to perform the adjustment. The compensation operation compensates for (or "undoes") a change related to an eye change, e.g., pupil center shift or pseudo-rotation. The compensation operation may be any suitable operation. For example, to compensate for a translational change (such as a pupil center shift), the compensation operation may apply the inverse of the translational change. As another example, to compensate for a rotational change (such as cyclotorsion), the compensation operation may apply the amount of the rotational change. As yet another example, a compensation operation may be adjusted to take into account an apparent change (such as pseudo-rotation) that is not part of an actual change.

In one case, a measured cyclotorsion may include pseudo-rotation. The pseudo-rotation may be subtracted from the measured cyclotorsion to determine the actual cyclotorsion. The compensation operation may then compensate for the actual cyclotorsion. As yet another example, the compensation operation may apply an inverse of both a translational and rotational change.

In certain embodiments, computing system 24 adjusts a laser treatment pattern, such as an ablation or photodisruption pattern. A laser treatment pattern describes a pattern of laser pulses that treat a condition of eye 12. An ablation pattern describes a pattern of laser pulses that yield a corneal shape that can reduce or correct refractive error. The ablation pattern may specify the amount of tissue to be removed as particular locations of the cornea in order to achieve the specific shape. A photodisruption pattern describes a pattern of laser pulses that yield a lenticule shape that can be removed to reduce or correct refractive error. A laser treatment pattern may be calculated using diagnostic data received from diagnostic device 20.

Computing system 24 adjusts a laser treatment pattern in any suitable situation. As an example, computing system 24 receives notification of eye movement and adjusts formation of the laser treatment pattern to compensate for the eye movement. As another example, computing system 24 receives a selection of a selected pupil size and adjusts formation of the laser treatment pattern for the selected pupil size.

Figure 2:
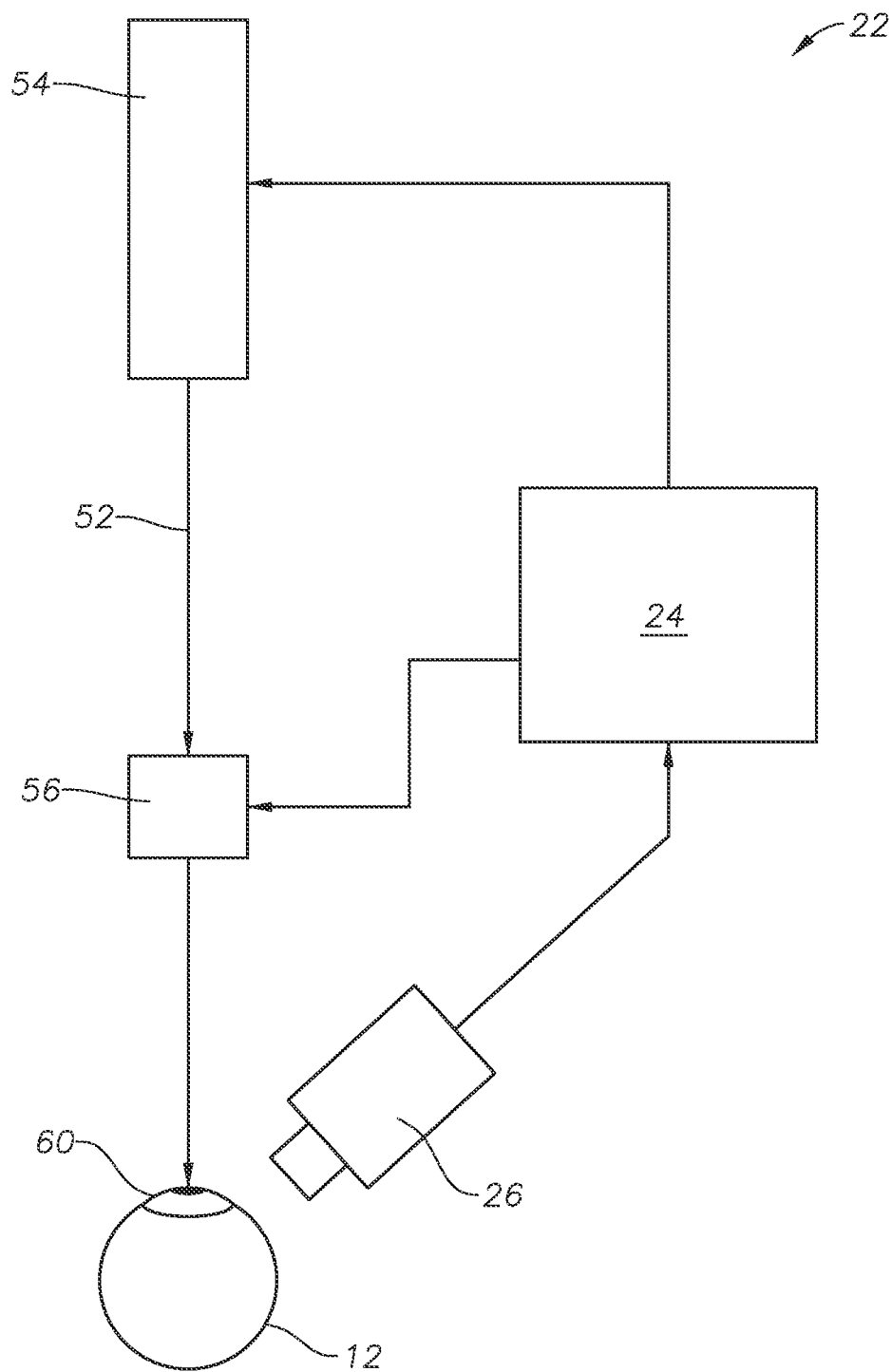
FIG. 2 illustrates an example of a surgical system that may be used with the system of FIG. 1 according to certain embodiments.

FIG. 2 illustrates an example of a surgical system 22 that may be used with system 10 of FIG. 1 according to certain embodiments. In the example, system 22 comprises a laser beam source 54, one or more optical elements 56, an optical recorder 26, and a computing system 24. In certain embodiments, laser beam source 54 emits a laser beam 52 that is shaped and guided by optical elements 56 towards a target, e.g., the cornea 60 of eye 12. Optical recorder 26 obtains optical data of features of eye 12 (e.g., the pupil, iris, and/or limbus) and sends the data to computing system 24.

Laser beam source 54 may be any suitable laser beam source that can emit a laser beam with laser pulses that can treat, e.g., photoablate or photodisrupt, a target, e.g., cornea 60. For example, laser beam source 54 may be an excimer laser or a femtosecond laser that emits a beam in the ultraviolet (UV) or infrared (IR) wavelength range. Optical elements 56 may comprise one or more elements that can operate on light, e.g., reflect, refract, diffract, and/or transmit light. Optical recorder 26 may be as described with reference to FIG. 1. Computing system 24 controls components, e.g., laser beam source 54 and optical elements 56 in accordance with a control program that includes computer code that instructs the components to focus the laser pulses at a region of the cornea 60 to ablate or disrupt at least a portion of the region. The laser pulses may be controlled to follow a laser treatment pattern to yield a desired shape.

Figure 3:
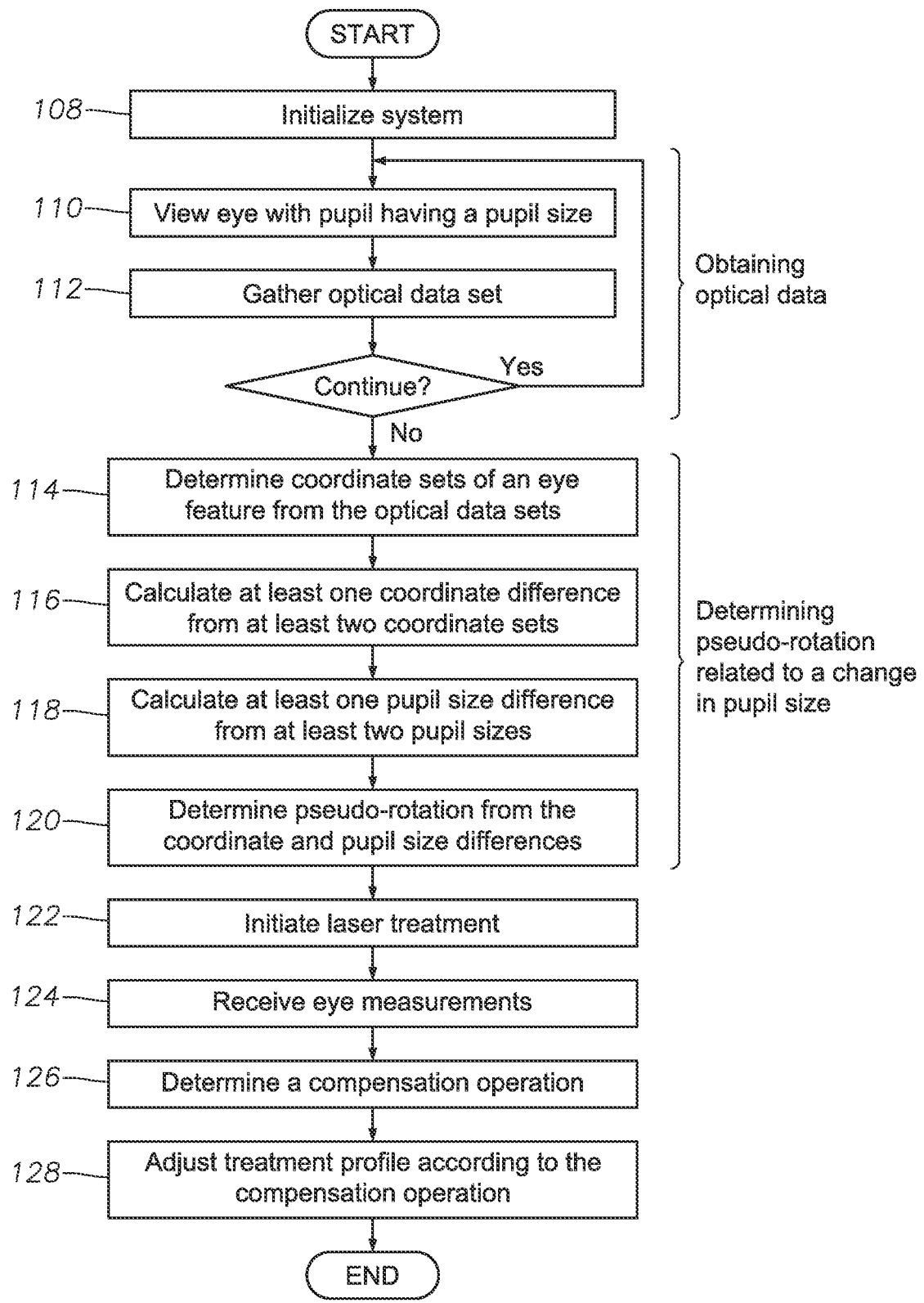
FIG. 3 illustrates an example of a method that may be performed by the system of FIG. 1 according to certain embodiments.

FIG. 3 illustrates an example of a method that may be performed by system 10 of FIG. 1 according to certain embodiments. In certain embodiments, the method may be performed by code 34 of computing system 24 of system 10.

System 10 is initialized to perform the method at step 108. Steps 110 and 112 describe obtaining optical data comprising at least two optical data sets. Optical recorder 26 views pupil 40 with a particular pupil size at step 110 and gathers an optical data set of eye 12 with that particular pupil size at step 112. Steps 110 and 112 yield an optical data set for a particular pupil size, and the steps may be repeated for a number of iterations in order to obtain any suitable number of optical data sets. For example, the steps may be repeated two times to obtain two optical data sets.

Steps 114 through 120 describe determining pseudo-rotation related to a change in pupil size. Coordinate sets of a feature of the eye 12 are determined from the optical data sets at step 114. A feature of eye 12 may be any suitable portion of eye 12 that can be recognized and/or captured by an optical recorder to determine pseudo-rotation. Examples of features include at least a portion of a limbus 44, at least a portion of an iris 42, a line of sight defined by the pupil center, an apex or vertex of a cornea 60, at least a portion of the sclera, one or more blood vessels, at least a portion of a pupil 40, and/or a pupil center. A coordinate set of a feature may be a set of coordinate values that indicate the location of the feature.

At least one coordinate difference is calculated from at least two (or more) coordinate sets at step 116. Different coordinate sets represent the locations of the feature when the pupil has different pupil sizes. Accordingly, a difference in the coordinate sets indicates a change in the feature that is related to the change in pupil size. A pupil size difference between the first pupil size and the second pupil size is calculated at step 118. Pupil size may be expressed with any suitable measurement, for example, as a pupil dimension or other feature. The pupil size difference may be the difference in the measurements. Pseudo-rotation is determined from the pupil size difference and the coordinate difference at step 120. In certain embodiments, a function that describes the eye feature movement that occurs with the pupil changes may be determined. The function may describe the relationship between a change in coordinates of the eye feature with respect to a change in the pupil size. The function may be calculated by curve-fitting a function (e.g., a linear function) that best describes the relationship. As an example, the function may be expressed as $f(\Delta c, \Delta s)=k$, where k is a constant, $\Delta s$ represents a change in pupil size from s1 to s2, $\Delta c$ represents a change in feature location from c1 to c2, c1 represents coordinates of an eye feature when the pupil size is s1, and c1 represents coordinates of the eye feature when the pupil size is s2.

Laser treatment is initiated at step 122. In certain embodiments, computing system 24 receives a selection of a pupil size for the treatment. The selected pupil size may be a user input, e.g., input from a surgeon, or may be the current size of the pupil as measured by optical recorder 26. In certain embodiments, laser system 28 performs the treatment only after receiving an indication that the pupil has the selected pupil size to ensure that the pupil is at the correct size for the treatment pattern.

Measurements of the eye are received at step 124. The measurements may indicate eye movement, such as cyclotorsion. A compensation operation is determined in response to the measurements at step 126. A cyclotorsion compensation operation that compensates for actual cyclotorsion may be determined. To determine actual cyclotorsion, the pseudo-rotation may be subtracted from the measured cyclotorsion. The compensation operation may then compensate for the actual cyclotorsion.

Computing system 24 adjusts the treatment profile according to the compensation operation at step 128. In certain embodiments, computing system 24 may apply the compensation operation that compensates for actual cyclotorsion. In certain embodiments, computing system 24 may perform the adjustment in real time. The method then ends.

Figure 4A:
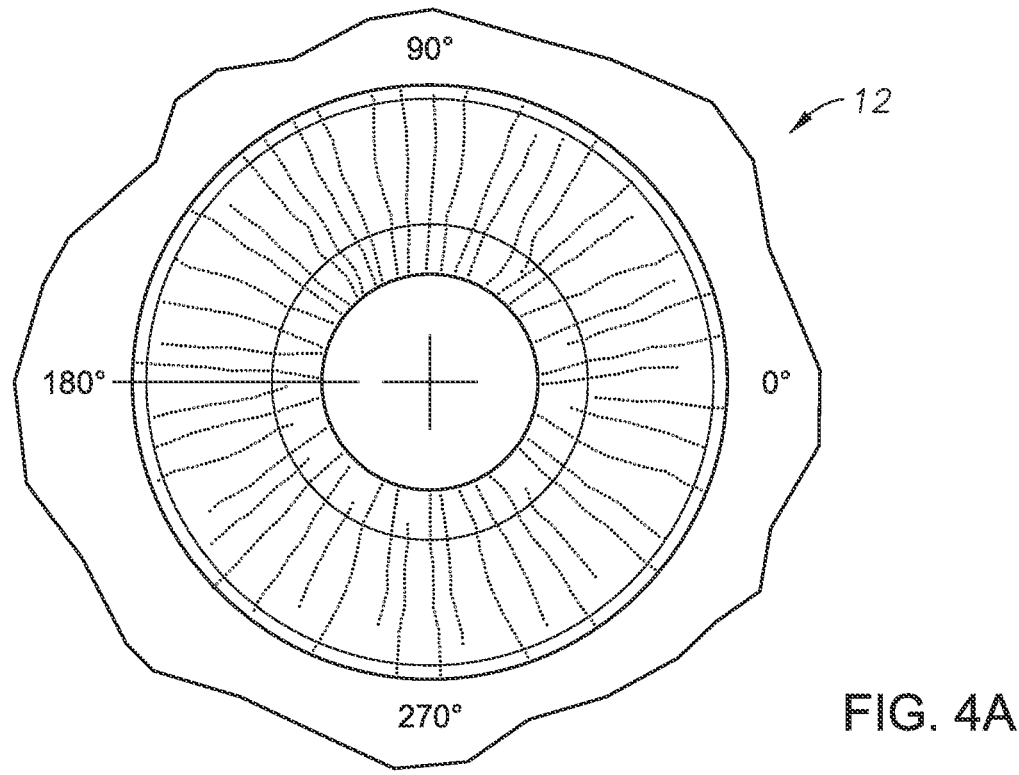
FIGS. 4A and 4B illustrate an example of cyclotorsion of an eye.
Figure 4B:
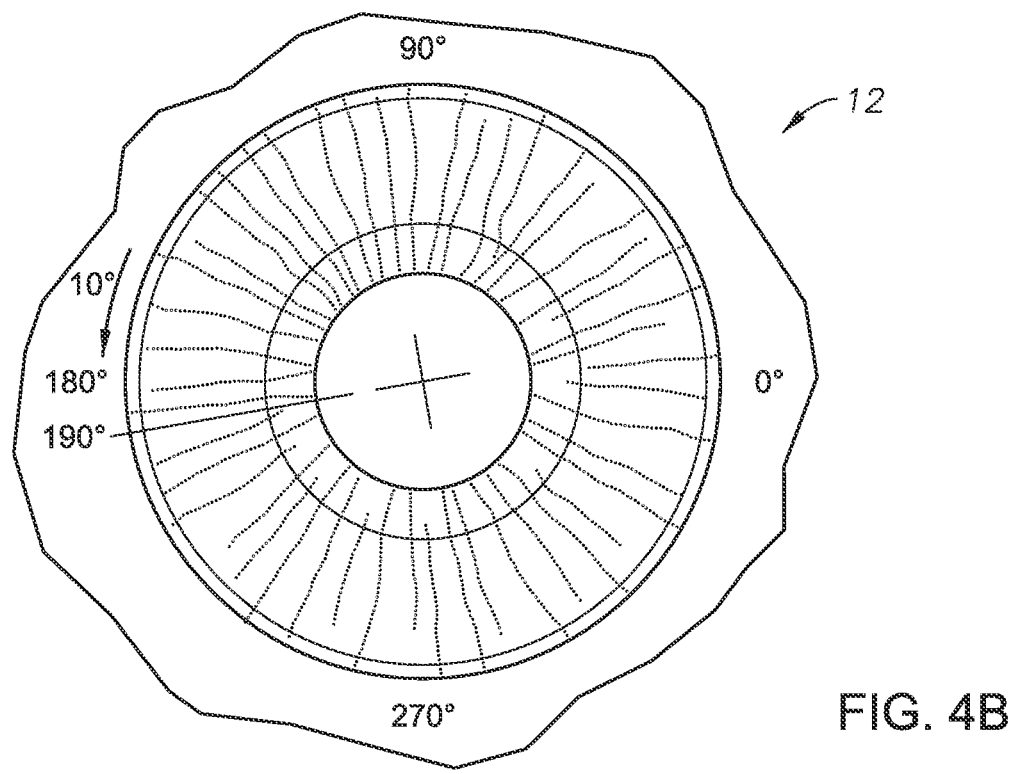

FIGS. 4A and 4B illustrate an example of cyclotorsion of an eye 12. FIG. 4A illustrates the eye 12 of a patient in one position, e.g., in a seated position. In the example, an x-axis of the eye 12 is at 180°. FIG. 4B illustrates the eye 12 of the patient in another position, e.g., in a recumbent position. In the example, the x-axis of the eye 12 has moved to 190°.

Figure 5A:
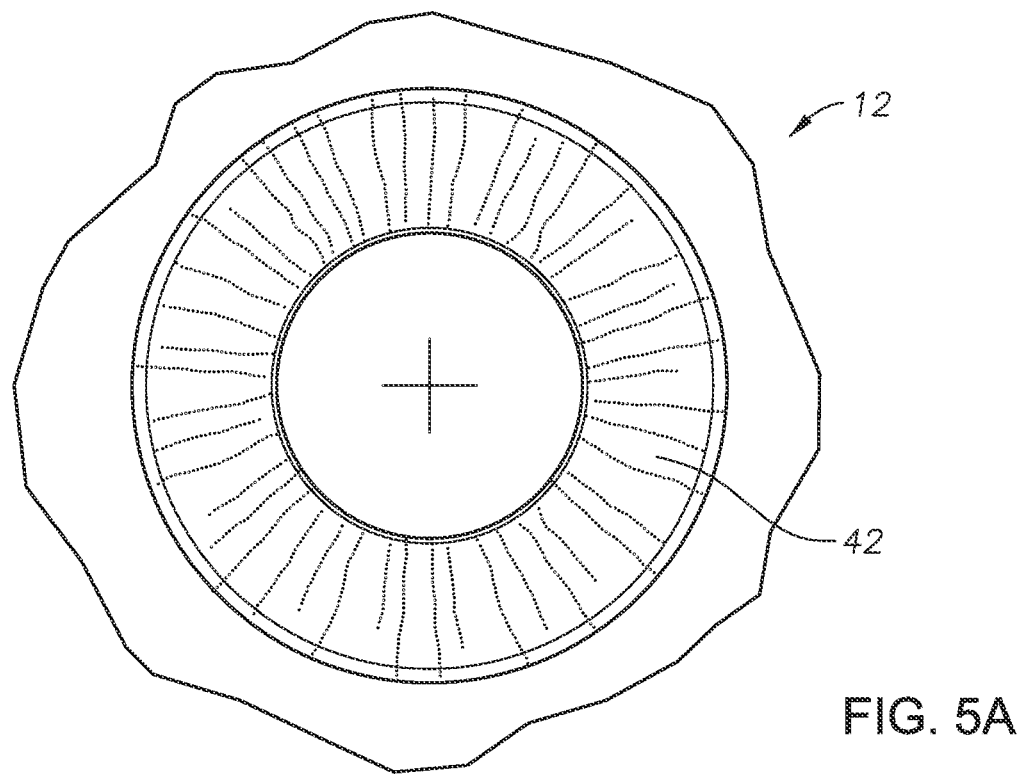
FIGS. 5A and 5B illustrate an example of pseudo-rotation of an eye.
Figure 5B:
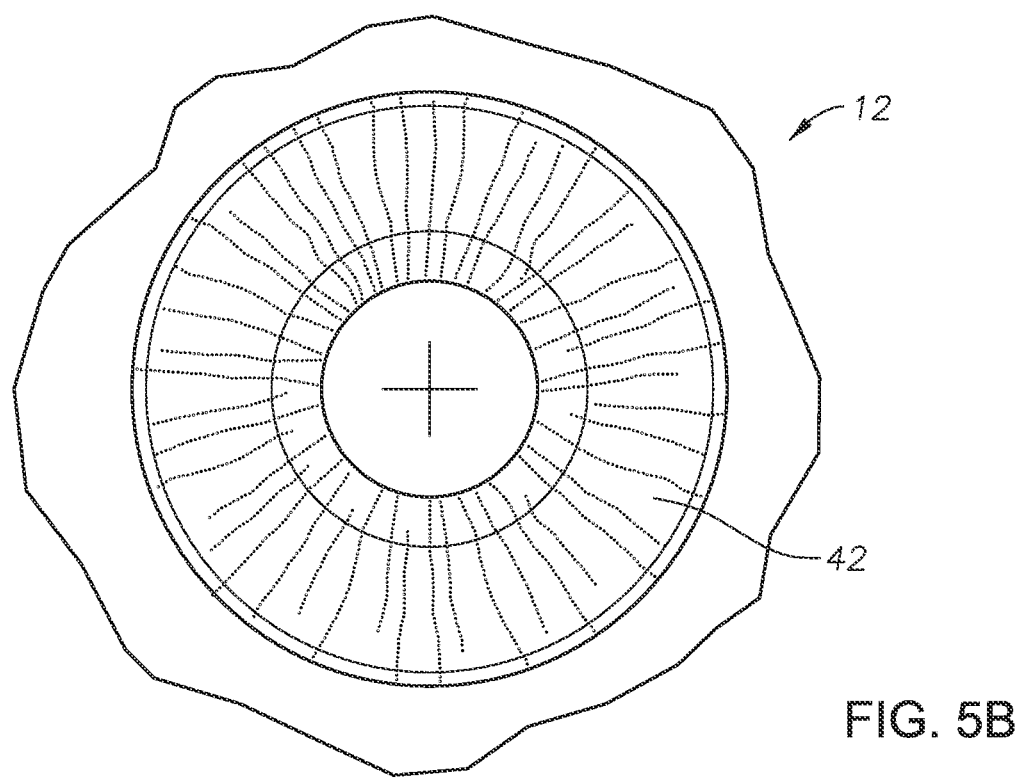

FIGS. 5A and 5B illustrate an example of pseudo-rotation of an eye 12. FIG. 5A may be an image taken under lower illumination, and FIG. 5B may be an image taken under higher illumination. As the iris 42 changes in response to different illumination, the eye 12 may appear to rotate, even though it actually does not rotate.

A component of the systems and apparatuses disclosed herein (e.g., computing system 24) may include an interface, logic, memory, and/or other suitable element, any of which may include hardware and/or software. An interface can receive input, send output, process the input and/or output, and/or perform other suitable operations. Logic can perform the operations of a component, for example, execute instructions to generate output from input. Logic may be encoded in memory and may perform operations when executed by a computer. Logic may be a processor, such as one or more computers, one or more microprocessors, one or more applications, and/or other logic. A memory can store information and may comprise one or more tangible, computer-readable, and/or computer-executable storage medium. Examples of memory include computer memory (for example, Random Access Memory (RAM) or Read Only Memory (ROM)), mass storage media (for example, a hard disk), removable storage media (for example, a Compact Disk (CD) or a Digital Video Disk (DVD)), database and/or network storage (for example, a server), and/or other computer-readable media.

In particular embodiments, operations of the embodiments may be performed by one or more computer readable media encoded with a computer program, software, computer executable instructions, and/or instructions capable of being executed by a computer. In particular embodiments, the operations may be performed by one or more computer readable media storing, embodied with, and/or encoded with a computer program and/or having a stored and/or an encoded computer program.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, and the operations of the systems and apparatuses may be performed by more, fewer, or other components. As another example, modifications may be made to the methods disclosed herein. The methods may include more, fewer, or other steps, and the steps may be performed in any suitable order.

Other modifications are possible without departing from the scope of the invention. For example, the description illustrates embodiments in particular practical applications, yet other applications will be apparent to those skilled in the art. In addition, future developments will occur in the arts discussed herein, and the disclosed systems, apparatuses, and methods will be utilized with such future developments.

The scope of the invention should not be determined with reference to the description. In accordance with patent statutes, the description explains and illustrates the principles and modes of operation of the invention using exemplary embodiments. The description enables others skilled in the art to utilize the systems, apparatuses, and methods in various embodiments and with various modifications, but should not be used to determine the scope of the invention.

The scope of the invention should be determined with reference to the claims and the full scope of equivalents to which the claims are entitled. All claims terms should be given their broadest reasonable constructions and their ordinary meanings as understood by those skilled in the art, unless an explicit indication to the contrary is made herein. For example, use of the singular articles such as "a," "the," etc. should be read to recite one or more of the indicated elements, unless a claim recites an explicit limitation to the contrary. As another example, "each" refers to each member of a set or each member of a subset of a set, where a set may include zero, one, or more than one element. In sum, the invention is capable of modification, and the scope of the invention should be determined, not with reference to the description, but with reference to the claims and their full scope of equivalents.

What is claimed is:

1. A method comprising:
    storing, by one or more memories, optical data from an optical recorder comprising at least two optical data sets by:
        gathering a first optical data set of an eye with a pupil having a first pupil size; and
        gathering a second optical data set of the eye with the pupil having a second pupil size;
    determining, by one or more processors, a pseudo-rotation related to a pupil size change, a pseudo-rotation being a fake rotation where the eye just appears to be rotating;
    receiving, by the one or more processors, a measured cyclotorsion, a cyclotorsion being a real or actual rotation of the eye;
    calculating, by the one or more processors, an actual cyclotorsion from the measured cyclotorsion and the pseudo-rotation by subtracting the pseudo-rotation from the measured cyclotorsion; and
    adjusting, by the one or more processors, a laser treatment to compensate for the actual cyclotorsion.

2. The method of claim 1, the determining the pseudo-rotation related to the pupil size change further comprising:
    determining a first coordinate set indicating a first location of a feature of the eye from the first optical data set;
    determining a second coordinate set indicating a second location of the feature of the eye from the second optical data set;
    calculating a coordinate difference between the first coordinate set and the second coordinate set; and
    calculating the pseudo-rotation using the coordinate difference.

3. The method of claim 2, the calculating the pseudo-rotation using the coordinate difference further comprising:
    calculating a pupil size difference between the first pupil size and the second pupil size; and
    determining the pseudo-rotation from the pupil size difference and the coordinate difference.

4. The method of claim 2, the calculating the pseudo-rotation using the coordinate difference further comprising:
    calculating a pupil size difference between the first pupil size and the second pupil size; and
    determining a function from the pupil size difference and the coordinate difference, the function describing a relationship between a change in the coordinates with respect to a change in the pupil size.

5. The method of claim 2, the feature of the eye comprising at least a portion of a limbus of the eye, at least a portion of an iris of the eye, an apex or vertex of a cornea of the eye, at least a portion of an iris of the sclera, one or more blood vessels, at least a portion of an iris of the pupil, or a pupil center of the eye.

6. The method of claim 1, further comprising:
    receiving a selection of a selected pupil size for the laser treatment; and
    determining a laser treatment pattern to perform the laser treatment for the selected pupil size.

7. The method of claim 6, wherein the selected pupil size is a user input.

8. The method of claim 6, wherein the selected pupil size is measured by the image recorder.

9. The method of claim 1, further comprising:
    performing the laser treatment only after receiving next optical data indicating that the pupil has a selected pupil size.

10. The method of claim 1, the image recorder comprising an eye-tracking device.

11. The method of claim 1, the adjusting the laser treatment according to the actual cyclotorsion further comprising:
    adjusting the laser treatment in real time.

12. A system comprising:
    one or more memories configured to store optical data from an optical recorder comprising at least two optical data sets by:
        receiving a first optical data set of an eye with a pupil having a first pupil size; and
        receiving a second optical data set of the eye with the pupil having a second pupil size; and
    one or more processors configured to:
        determine a pseudo-rotation related to a pupil size change, a pseudo-rotation being a fake rotation where the eye just appears to be rotating;
        receive a measured cyclotorsion, a cyclotorsion being a real or actual rotation of the eye;
        calculate an actual cyclotorsion from the measured cyclotorsion and the pseudo-rotation by subtracting the pseudo-rotation from the measured cyclotorsion; and
        adjust a laser treatment to compensate for the actual cyclotorsion.

13. The system of claim 12, the determining the pseudo-rotation related to the pupil size change further comprising:
    determining a first coordinate set indicating a first location of a feature of the eye from the first optical data set;
    determining a second coordinate set indicating a second location of the feature of the eye from the second optical data set;
    calculating a coordinate difference between the first coordinate set and the second coordinate set; and
    calculating the pseudo-rotation using the coordinate difference.

14. The system of claim 13, the calculating the pseudo-rotation using the coordinate difference further comprising:
    calculating a pupil size difference between the first pupil size and the second pupil size; and
    determining the pseudo-rotation from the pupil size difference and the coordinate difference.

15. The system of claim 13, the calculating the pseudo-rotation using the coordinate difference further comprising:
    calculating a pupil size difference between the first pupil size and the second pupil size; and
    determining a function from the pupil size difference and the coordinate difference, the function describing a relationship between a change in the coordinates with respect to a change in the pupil size.

16. The system of claim 13, the feature of the eye comprising at least a portion of a limbus of the eye, at least a portion of an iris of the eye, an apex or vertex of a cornea of the eye, at least a portion of an iris of the sclera, one or more blood vessels, at least a portion of an iris of the pupil, or a pupil center of the eye.

17. The system of claim 12, the one or more processors further configured to:
   receive a selection of a selected pupil size for the laser treatment; and
   determine a laser treatment pattern to perform the laser treatment for the selected pupil size.

18. The system of claim 17, wherein the selected pupil size is a user input.

19. The system of claim 17, wherein the selected pupil size is measured by the image recorder.

20. The system of claim 12, the one or more processors further configured to:
   perform the laser treatment only after receiving next optical data indicating that the pupil has a selected pupil size.

21. The system of claim 12, the image recorder comprising an eye-tracking device.

22. The system of claim 12, the adjusting the laser treatment according to the actual cyclotorsion further comprising:
   adjusting the laser treatment in real time.

* * * * *